(12) United States Patent
Sarma et al.

(10) Patent No.: US 7,381,527 B2
(45) Date of Patent: *Jun. 3, 2008

(54) METHOD OF DETECTION OF SP-A2 GENE VARIANTS

(75) Inventors: Puranam Usha Sarma, Delhi (IN); Taruna Madan, Delhi (IN); Shweta Saxena, Delhi (IN)

(73) Assignee: Council of Scientific and Industrial Research (IN)

( * ) Notice: Subject to any disclaimer, the term of this patent is extended or adjusted under 35 U.S.C. 154(b) by 724 days.

This patent is subject to a terminal disclaimer.

(21) Appl. No.: 10/289,163

(22) Filed: Nov. 6, 2002

(65) Prior Publication Data

US 2004/0091868 A1    May 13, 2004

(51) Int. Cl.
*C12Q 1/68* (2006.01)
*C12P 19/34* (2006.01)
*C07H 21/04* (2006.01)

(52) U.S. Cl. .................. 435/6; 435/91.2; 536/24.33

(58) Field of Classification Search ............... 435/91.2, 435/6; 536/24.33
See application file for complete search history.

(56) References Cited

OTHER PUBLICATIONS

Madan et al. Association of polymorphisms in the collagen region of human SP-A2 genes with pulmonary tuberculosis in Indain population. Clin. Chem Lab Med., vol. 40(10), pp. 1002-1008, 2002.*

* cited by examiner

*Primary Examiner*—Suryaprabha Chunduru
(74) *Attorney, Agent, or Firm*—Reed Smith LLP; Nanda P. B. A. Kumar, Esq.; Jeanine A. Graham, Esq.

(57) ABSTRACT

The invention provides a method for predicting the susceptibility of an individual to pulmonary tuberculosis, the method comprising amplifying genomic DNA of pulmonary tuberculosis patients and normal control individuals using oligonuecleotide primers, sequencing the amplified PCR product and identifying the sequence variation computationally by comparing it with the already existing sequence of human SP-A2 gene.

3 Claims, 2 Drawing Sheets

| G/C CT |         | AG  A/G |

FIGURE 2

| G/C CT |         | AG  A/G |

FIGURE 3

METHOD OF DETECTION OF SP-A2 GENE VARIANTS

FIELD OF THE INVENTION

The present invention relates to a method for predicting the susceptibility of an individual to pulmonary tuberculosis. The utility of the invention lies in applications such as molecular diagnosis, prediction of an individual to disease susceptibility and genetic analysis of a population for pulmonary tuberculosis. The invention also provides primer sequences useful in detecting polymorphic variations in the SP-A2 gene and their use in diagnosis and prediction of an individual's susceptibility to pulmonary tuberculosis.

BACKGROUND AND PRIOR ART

About the Disease and Pulmonary Surfactant Protein A

Tuberculosis (TB) is caused by *Mycobacterium tuberculosis* [Grange J M and Bishop P J. A tribute to Robert Kosh's discovery of the tubercle bacillus. 'UberTuberkulosis' 1982; 62:1-17]. *M. bovis* and *M. africanum* which are closely related organisms, can also infect human beings [Young L S. Mycobacterial diseases and the compromised host. Clin Infect Dis 1993; 17:8436-8441]. In addition, there are other human pathogens belonging to the genus *Mycobacterium* which are related to *M. tuberculosis*, such as *M. avium* and *M. leprae*, that represent important pathogens.

There is a growing concern about the worldwide increasing incidence of TB, a leading killer disease [Raviglione M C, Snider D E Jr, Kochi A. Global epidemiology of tuberculosis. Morbidity and mortality of a worldwide epidemic. JAMA 1995; 273:220-6]. It kills three million people all over the world annually. One third of the world population is estimated to be infected with *M. tuberculosis* asymptomatically, and in the year 1995, more people died of TB than in any earlier year in the history of mankind [Kochi A. WHO report on tuberculosis epidemic. 1996].

According to a recent report by WHO on tuberculosis epidemic (WHO Annual Report, 2000), it is estimated that between 2000 and 2020, nearly one billion people will carry the tuberculosis bacteria, 200 million people waaill get sick, and 35 million will die of TB, if control and preventive measures are not strengthened.

Tuberculosis primarily affects lungs (Pulmonary tuberculosis), although in one-third of the cases other organs are also affected. It is mainly transmitted by patients with infectious pulmonary tuberculosis in the form of airborne droplet nuclei produced during coughing and sneezing [Riley R L and Grady F O. Airborne infection. Transmission and control. The Macmillan Co., New York. 1961]. The disease, if untreated, can be fatal within a few years.

*Mycobacterium tuberculosis* is a facultative intracellular pathogen of alveolar macrophages located in the apical region of lung [Balasubramanian V, Weigeshaus E H, Taylor B T, Smith D W. Pathogenesis of tuberculosis: pathway to apical localization. Tuber Lung Dis 1994; 75:168-78]. It employs several mechanisms to enter human macrophages, where it survives well and from where it continues its pathogenic life cycle. Innate immune system is an integral part of host defense against tuberculosis [Schluger N W, Rom W N. The host immune response to tuberculosis. Am J Respir Crit Care Med 1998; 157:679-91]. Pulmonary surfactant, especially surfactant proteins A and D, has evolved as an important component involved in innate immunity as well as regulation of inflammatory processes of the lung [Mason R J, Greene K, Voelker D R. Surfactant protein A and surfactant protein D in health and disease. Am J Physiol 1998; 275:L1-13].

Human lung surfactant protein A (SP-A) binds *M. tuberculosis* and enhances attachment of *M. tuberculosis* to alveolar macrophages [Gaynor C D, McCormack F X, Voelker D R, Me Gowan S E, Schlesinger L S. Pulmonary surfactant protein A mediates enhanced phagocytosis of *Mycobacterium tuberculosis* by a direct interaction with human macrophages. J Immunol 1995; 155:5343-51.; Pasula R, Downing J F, Wright J R, Kachel D L, Davis T E Jr, Martin W J 2IX-Surfactant protein A (SP-A) mediates attachment of *Mycobacterium tuberculosis* to murine alveolar macrophages. Am J Respir Cell Mol Biol 1997; 17:209-17]. SP-A has also been implicated as an opsonin enhancing phagocytosis of mycobacteria by alveolar macrophages [Weikert L F, Edwards K, Chroneos Z C, Hager C, Hoffman L, Shepherd V L. SP-A enhances uptake of bacillus Calmette-Guerin by macrophages through a specific SP-A receptor. Am J Physiol 1997; 272:L989-95].

In view of the importance of SP-A in host defense against tuberculosis, structural and functional changes in SP-A may affect the outcome of host-pathogen interaction.

SP-A is the major non-serum pulmonary surfactant-associated protein with 18 functional units showing significant structural similarity to Clq [Crouch E C. Collectins and pulmonary host defense Am J Respir Cell Mol Biol 1998 19:177-201]. The human genome contains two highly similar SP-A genes (SP-A1 and SP-A2) and a pseudogene that corresponds to 3' half of the SP-A1 gene [Hoover R R, Floras J. Organization of the human SP-A and SP-D loci at 10q22-q23. Physical and radiation hybrid mapping reveal gene order and orientation. Am J Respir Cell Mol Biol 1998; 18:353-62].

In adult human lung tissue, the ratio of SP-A2 to SP-A1 mRNA transcripts has been observed to be 3:1 [McCormick S M, Boggaram V, Mendelson C R. Characterization of mRNA transcripts and organization of human SP-A1 and SP-A2 genes. Am J Physiol 1994; 266:L354-66]. Contributions of SP-A 1 and SP-A2 genes to the SP-A transcript vary at different gestation times and SP-A2 gene is more responsive to glucocorticoids [Kumar A R, Snyder J M. Differential regulation of SP-A1 and SP-A2 genes by cAMP, glucocorticoids, and insulin. Am J Physiol 1998; 274:L177-85].

For each human SP-A gene, based on sequence differences within the coding region more than 30 genetic variants (alleles) have been reported [DiAngelo S, Lin Z, Wang G, Phillips S, Ramet M, Luo J, Floras J. Novel, non-radioactive, simple and multiplex PCR-cRFLP methods for genotyping human SP-A and SP-D marker alleles. Dis Markers 1999; 15:269-81]. Some of the allelic variants of SP-A1 and SP-A2 have been associated with respiratory diseases such as Respiratory distress syndrome (RDS) and Chronic obstructive pulmonary disease (COPD) [Karinch A M, deMello D E, Floros J. Effect of genotype on the levels of surfactant protein A mRNA and on the SP-A2 splice variants in adult humans. Biochem J 1997; 321:39-47; Kala P, Ten Have T, Nielsen H, Dunn M, Floros J. Association of pulmonary surfactant protein A (SP-A) gene and respiratory distress syndrome: interaction with SP-B. Pediatr Res 1998; 43:169-77; Ramet M, Haataja R, Marttila R, Hamalainen A M, Knip M, Hallman M. Human surfactant Protein~A gene locus for genetic studies in the Finnish population. Dis Markers 2000; 16:119-24; Guo X, Lin H M, Lin Z, Montano M, Sansores R, Wang G, DiAngelo S, Pardo A, Selman M, Floros J. Polymorphisms of surfactant protein gene A, B, D, and of SP-B-linked microsatellite markers in COPD of a Mexican population. Chest 2000; 117:2498-508].

A recent case-control association study showed that the frequency of certain alleles of SP-A is increased in individuals with tuberculosis in Mexican population [Floros J, Lin H M, Garcia A, Salazar M A, Guo X, DiAngelo S, Montano M, Luo J, Pardo A, Selman M. Surfactant protein genetic marker alleles identify a subgroup of tuberculosis in a Mexican population. J Infect Dis 2000; 182:1473-8]. However, the allelic variants of SP-A1 and SP-A2 have not been identified so far in developing nations like India where pulmonary tuberculosis is highly prevalent. Collagen region of SP-A has been shown to be involved in receptor binding on macrophages, regulation of surfactant secretion and lipid uptake by type II cells [McCormack F X, Damodarasamy M, Elhalwagi B M. Deletion mapping of N-terminal domains of surfactant protein A. The N-terminal segment is required for phospholipid aggregation and specific inhibition of surfactant secretion. J Biol Chem 1999; 274:3173-81]. Two of the SNPs (1649 C/G and 1660 A/G) in the collagen region have shown association with patients of allergic bronchopulmonary aspergillosis [U.S. patent application Ser. No. 10/102, 731].

Disease Loci Identified Till Now and Their Associations

Association studies involve typing a genetic polymorphism in a large number of unrelated individuals with the disease of interest and a group of healthy ethnically matched controls. Genes which could be involved in the development of tuberculosis are HLA, Nrampl, Tumor Necrosis Factor, mannose binding protein, Vitamin D receptor, Interferon-y receptor, Interleukin 10, Interleukin 1α, 1β and RA, Complement receptor 1, 1C AMI, Fucosyltransferase 2, Inducible nitric oxide synthase, Chemokine receptors, Interleukin 4, Tfy cluster and Interleukin 6 etc. All these candidate gene contain known polymorphisms but there may be many other genes which could play a role in tuberculosis susceptibility and are worthy of investigation [Richard Bellamy. Genetic susceptibility to tuberculosis in human populations. Thorax 1998; 53: 588-593.].

Attempts to identify the actual gene involved in host susceptibility to tuberculosis have recently focussed on the human leucocyte antigen (HLA) systems. Associations have been found between the class I HLA antigens A10 and B8 and with the class II antigens DR2 [Brahmajothi V, Pitchappan R M, Kakkanaiah V N, et al The association of tuberculosis and HLA in South India. Tubercle 1991; 72: 123-32; Singh S P N, Mehra N K, Dingley H B, et al Human leucosyte antigen (HLA)-linked control of susceptibility to tuberculosis and association with HLA-DR types. J Infect Dis 1983; 148:676-81]. However, these associations have not been consistently demonstrated [Cox R A, Down M, Neimes R E, et al Immunogenetic analysis of human tuberculosis. J Infect Dis 1988; 158: 1302-8] and could account for only a small part of the significant genetic component in tuberculosis susceptibility identified by the twin study.

Frequency comparisons of surfactant protein marker alleles in tuberculosis patients and healthy controls subjects have also been performed. Regression analysis of the tuberculosis and the tuberculin-skin test positive groups revealed, on the basis of odds ration, tuberculosis susceptibility (DA11_C and GATA 3) and protective (AAGG__2) marker alleles. Similarly, 1 A$^3$,6A$^4$, and B1013_A and protective AAGG__2, and AAGG__7 marker alleles were observed. Moreover, interactions were seen between alleles 6A$^2$ and 1 A$^3$ and between 1A$^3$ and B1013_A. The findings indicate a possible involvement of SP alleles in tuberculosis pathogenesis [Joanna Floros, Hung-Mo Lin, Andrea Garcia, Miguel Angel Salazar, Xiaoxuan Guo, Susan DiAngelo, Martha Montano, Junming Luo, Annie Pardo, and Moises Selman. Surfactant Protein Genetic Marker Alleles Identify a Subgroup of Tuberculosis in a Mexican Population. J Infect. Dis. 2000; 182: 1473-8].

Single Nucleotide Polymorphisms

SNP's occur with greater frequency and are spaced more uniformly throughout the genome than other forms of polymorphism. The greater frequency and uniformity of SNP's means that there is a greater probability that such a polymorphism will be found in close proximity to a genetic locus of interest than would be the case for other polymorphisms. Also, the different forms of characterised SNP's are often easier to distinguish than other types of polymorphisms (eg. by use of assays employing allele-specific hybridisation probes or primers).

The Applicant after much research and study has demonstrated the application of SNP's (G1649C and A1660G) in human SP-A2 gene for use as molecular diagnosis and prediction of an individual's disease susceptibility to pulmonary tuberculosis, and/or the genetic analysis of SP-A2 gene in Indian population. The novelty of the present invention is in providing a method for detecting and associating allelic variants of SP-A2 gene with the disease and for prediction of an individual's predisposition to pulmonary tuberculosis.

OBJECTS OF THE INVENTION

The main object of the present invention is to provide a method for screening individuals carrying SP-A2 alleles predisposed to pulmonary tuberculosis.

Another object of the invention is to provide a method for establishing association of SPA2 allelic variants with susceptibility to pulmonary tuberculosis.

SUMMARY OF THE INVENTION

The present invention relates to allelic variants of human SP-A2 gene and provides specific primers suitable for detecting these allelic variants for applications such as molecular diagnosis, prediction of susceptibility of an individual to pulmonary tuberculosis, and/or the genetic analysis of SP-A2 gene in a population.

DETAILED DESCRIPTION OF THE INVENTION

The present invention relates to the detection of allelic variants of the human SP-A2 gene and their utility in predicting an individual's susceptibility to pulmonary tuberculosis. Accordingly, the present invention provides method for detection of human SP-A2 gene variants, said method comprising the steps of:
  a) amplifying genomic DNA of pulmonary tuberculosis patients and of normal control individuals using oligonucleotide primers for PCR amplification of the polymorphic site containing A or G base region containing exon-4 to obtain an amplified product,
  b) sequencing the amplified PCR product and identifying the sequence variation computationally by comparing it with human SP-A2 gene,
  c) establishing the association of C and G haplotypes as defined by the nucleotide present at position 1649 and 1660, with pulmonary tuberculosis, based on the haplotype frequency distribution in normal individuals and tuberculosis patients, and d) predicting the risk or susceptibility to pulmonary tuberculosis based on the haplotype present at the polymorphic sites in the said individual, wherein a haplotype with C at 1649 position and A at 1660 position is at low risk and a haplotype with G at 1649 position and G at 1660 position is at high risk for the disease.

As such, the invention provides a method for predicting the susceptibility of an individual to pulmonary tuberculosis, which comprises:

(a) amplifying the genomic DNA of pulmonary tuberculosis patients and normal control individuals using the primers (SEQ ID 1,2,3,4), (b) Sequencing the amplified PCR product and identifying sequence variation computationally by comparing it with the already reported sequence of human SP-A2 gene (accession No. M68519), (c) screening normal control individuals and pulmonary tuberculosis patients for novel single nucleotide polymorphisms by sequencing amplified exon 4 of SP-A2 gene, (d) computing the frequencies of G/C alleles (SNP at position 1649) and A/G alleles (SNP at position 1660) in normals and pulmonary tuberculosis patients, (e) establishing the association of G/C and A/G alleles with the pulmonary tuberculosis disease based on their frequencies distribution on normal and pulmonary tuberculosis patients, and (f) predicting the resistance or susceptibility to the pulmonary tuberculosis based on the nucleotide present at the polymorphic sites in the individual tested. wherein individuals with C allele (at nucleotide position 1649) and A allele (at nucleotide position 1660) are at low risk and those with G allele (at nucleotide position 1649) and G allele (at nucleotide position 1660) are at high risk to the disease.

In an embodiment, the primers suitable for amplification of SP-A2 gene region containing one or more polymorphic sites, all selected from the group consisting of SEQ ID No: 1, SEQ ID No:2, SEQ ID No. 3, SEQ ID No. 4 & compliments thereof.

primers and probes selected from polynucleotide sequences under SEQ ID No. 1-4. The kit may contain additional buffers or other accessories suitable for identification of SP-A2 gene variants and establishing an individual's susceptibility to pulmonary tuberculosis.

In another embodiment of the invention an eukaryotic expression vector containing the allelic variants of SP-A2 gene is provided.

The allelic variants of human SP-A2 gene may comprise one or more of the following SNP's as compared with the human SP-A2 complete cDNA sequence in the database (GenBank Accession No. M68519)

The site of change is in accordance with the human SP-A2 complete cDNA sequence in the database (GenBank Accession No. M68519).

The invention also provides a method of analysing a nucleic acid from an individual for the presence of base at anyone of the polymorphic site shown in Table-I. This type of analysis can be performed on a plurality of individuals who are tested either for the presence or for predisposition to pulmonary tuberculosis. The susceptibility to the disease can then be established based depending on the base or set of bases present at the polymorphic sites in the individuals tested.

TABLE I

| | Site of change | Base change | Amino acid alteration |
|---|---|---|---|
| A | Nucleotide position 1649 | G-C | Alanine- Proline |
| B | Nucleotide position 1660 | A-G | Arginine- Arginine |

Eukaryotic expression vectors comprising a DNA sequence coding for a protein or a peptide according to the invention are new materials and also included in the invention.

Host cells, for example cloned human cell lines, can be transformed using the new expression vectors and are also included in the invention.

The region containing the SNP's was PCR amplified using the primers SP-A2 F and SPA2 R. Approximately 100 ng of genomic DNA was amplified in a 50 nl reaction

```
SEQ ID 1 - 5' CTG CGT GCG AAG TGA AGG ACG TTT GTG TTG 3'   (Forward)

SEQ ID 2 - 5' GAC CCC CAT CAC CCC TGT GTA ACT GAC TTC 3'   (Reverse)

SEQ ID 3 - 5' TGC CTG GAG CCC CTG GTG TCC CTG GAG AGC 3'   (Forward)

SEQ ID 4 - 5' TGC CTC GTC CGC ATT CAC CCT TCA GAC TGC 3'   (Reverse)
```

These primers can be used as allelle specific primers and are suitable for detection of the polymorphic sites.

In still another embodiment, allelic variants of SP-A2 gene have G/C and A/G haplotypes.

G/C CT

AG A/G

Further, the invention provide a diagnostic kit for the detection of SNP haplotypes C/G or A/G comprising suitable volume containing a final concentration of 5 mM Tris, 25 mM KCl, 0.75 mM magnesium chloride ($MgCl_2$), 0.05% gelatin, 20 pM of each primer and 1.5 U of Taq DNA polymerase. Samples were denatured at 95° C. for 5 min followed by 30 cycles of denaturation (95° C. for 1 min), annealing (70° C., 1 min), extension (72° C., 1 min) and a final extension of 7 min at 72° C. in a Perkin Elmer Gene Amp PCR System 9600. The PCR product was purified from band cut out of the agarose gel using QIA Quick gel extraction kit (QIAGEN) and was sequenced using dye terminator chemistry on an ABI Prism 377 automated DNA sequences with the PCR primers.

BRIEF DESCRIPTION OF THE DRAWINGS

The manner in which the above-mentioned features, advantages and objects of the invention as well as others which will become clear are attained and can be understood in details by the particular description of the invention are illustrated in the appended drawings, however, that the appended drawings illustrate preferred embodiments of the invention and thereof not be considered limiting in their scope.

In the drawings, accompanying the specifications—

Figures 2, 3:
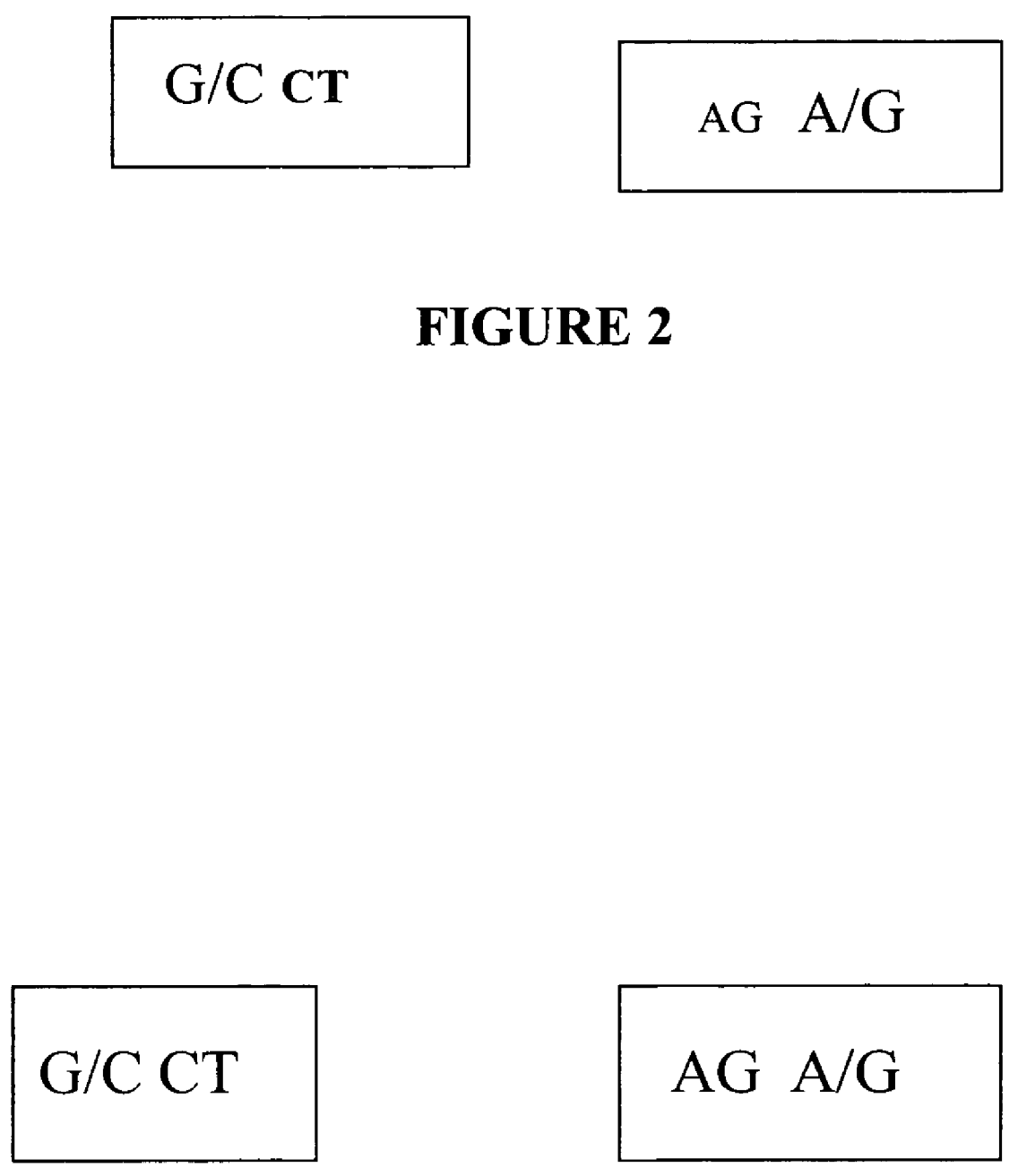

FIG. 2 is a block diagram to illustrate SNP's (G1649C and A1660G) in human SP-A2 gene.

FIG. 3 is a block diagram to show that allelic variants of SP-A2 gene have C/G and A/G haplotypes.

Figure 1:
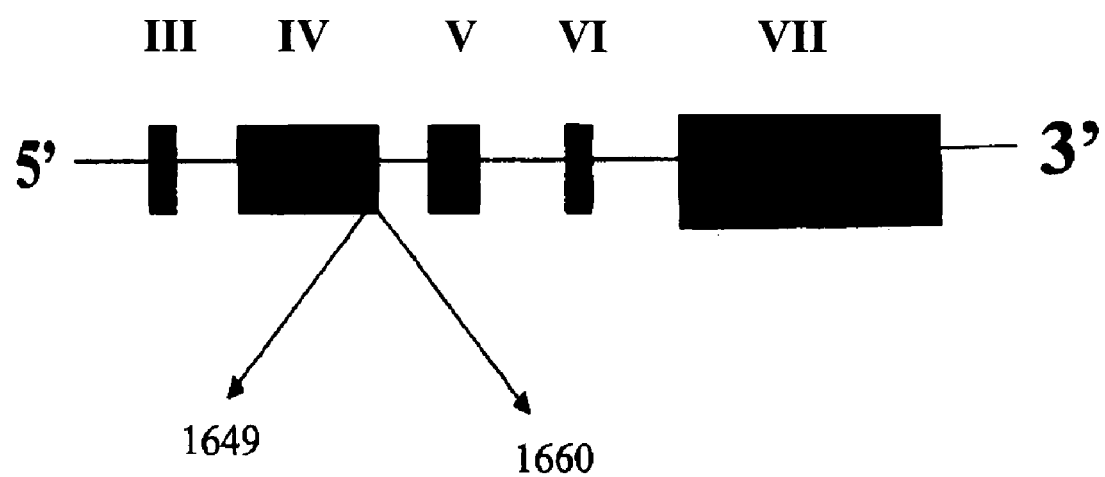
FIG. 1 is a schematic representation of the two SNP's in SP-A 2 gene. The top line depicts the position of the four exons of the SP-A2 gene. The second line shows the relative locations of the two polymorphic sites. Both the polymorphisms are also shown in the sequence content of the gene.

Other and further aspects, features, and advantages of the present invention will be apparent from the following description of the preferred embodiments of the invention given for the purpose of disclosure. Alternative embodiments of the invention can be envisaged by those skilled in the art. All such alternative embodiments are intended to lie within the scope of this invention.

I. Polymorphism in the SP-A2 Gene

As a first step to the present invention, the applicants carried out the PCR amplification of exon 4 of human SP-A2 complete cDNA sequence submitted by Katyal et. al. in the database (Katyal, S. L., Singh, G. and Locker, characterization of a second human pulmonary surfactant-associated protein SP-A gene. Am. J. Respir. Cell Mol. Biol. 1992; 6: 446-452) (GenBank Accession No. M68519). The sequencing of the purified PCR product revealed two SNP's in the exon 4 of human SP-A2 gene.

The present invention provides a sequence for the allelic variants of human SP-A2 gene comprising one or more of the following SNP's compared with the human SP-A2 complete cDNA sequence in the database.

The site of change is in accordance with the human SP-A2 complete cDNA sequence in the database (GenBank Accession No. M 68519).

The first polymorphic site (A) as shown in FIG. 1, had either a C or a G. The second polymorphic site (B) contains either an A or a G base. While the first substitution changes the amino acid sequence from Proline to Alanine, the second substitution is neutral. For example, the nucleotide sequence of the allelic variant of exon 4 of human SP-A2 gene having polymorphic sites as listed in table-I may be: 5' gccccatggg tccgcctgga gaaacaccat gtcctcctgg gaataatggg ctgcctggag cccctggtgt ccctggagag cgtggagaga aggggagCc tggcgagagg ggccctccag 3' (SEQ ID NO:5).

In the above sequence, the SNP's (A) and (B) are at nucleotide position 1649 and 1660 respectively and are in bigger and bold font. The above sequence is denoted as Sequence ID NO: 5.

II. Association Analysis with the Disease

Analysis of these two SNP's in the 19 Normal and 17 pulmonary tuberculosis patient chromosomes revealed that two haplotypes, possible with each SNP in a biallelic polymorphic system, were observed. The frequency in Normal and ABPA patient chromosome is summarised in Table-II.

Further, studies on pulmonary tuberculosis patient chromosomes revealed a high significant difference in the distribution of the two SNP's in the normal and the pulmonary tuberculosis patient chromosome (Table-II).

TABLE II

| | No. of chromosomes (N) studied | SNP at 1649 position | | SNP at 1660 position | |
|---|---|---|---|---|---|
| 1 | | % C allele | % G allele | % A allele | ^WS allele |
| Normal | 38 | 71.1 | 28.9 | 94.7 | 5.3 |
| Pulmonary tuberculosis | 34 | 61.1 | 38.2 | 67.6 | 32.4 |

III Diagnostic Kit

The invention further provides diagnostic kit, comprising at least one or more allele specific oligonucleotides as described in SEQ ID 1-4. Often the kit contain one or more pair of allele amplifying primers comprising two different forms of polymorphisms. Optional additional components of the kit includes, for example, restriction enzymes, reverse transcriptase or polymerase, the substrate nucleoside triphosphate, means use to label (for example, an evident enzyme conjugate and enzyme substrate and chromogen if the label is biotin) and the appropriate buffer for the reaction, PCR, or hybridisation reaction. Usually, the kit also contains instructions for carrying out the methods.

IV. Nucleic Acid Vectors

Variant genes can be expressed in an expression vector in which a variant gene is operably linked to a native or other promoter. Usually the promoter is a eukaryotic promoter for expression in mammalian cell. The transcription regulation sequence typically include a heterologous promoter and optionally an enhancer which is recognised by the test. The structure of an appropriate promoter, for example, Trp, Lac, phage promoter, glycolytic enzyme promoters and tRNA promoter depends on the host selected. Commercially available expression vectors can also be used. Suitable host cells include bacteria such as $E.\ coli$, Yeast, filamentous fungi, insect cells, mammalian cells, typically immortalised example, mouse, CHO, human and monkey cell lines and derivatives thereof. Preferred host cells are able to process the variant gene product to produce an appropriate mature polypeptide.

The invention further provides transgenic, non-human animals, capable of expressing an endogenous variant gene and/or having one or both allele of an endogenous variant gene inactivated. Expression of an endogenous variant gene is usually achieved by operably linking the gene to a promoter and optionally an enhancer, and microinjecting the construct into a zygote. Inactivation of endogenous variant genes can be achieved by forming a transgene in which a cloned variant gene is then introduced into an embryonic stem cell, where it undergoes homologous recombination with an endogenic variant gene. Mice and other rodents are preferred animals. Such animals provide useful drug delivery systems.

The invention is illustrated by the following examples which are given by the way of illustration of the present invention and should not be construed to limit the scope of the present invention.

EXAMPLE 1

Identification of Allelic Variants of SP-A2 Gene

This example describes the identification of allelic variant of human surfactant protein A 2 gene by PCR and sequencing using certain oligonucleotide primers. According to the invention DNA was extracted from human peripheral blood leukocytes using a modification of salting out procedure. The concentration of the DNA was determined by measuring the optical density of the sample, at a wavelength of 260 nm. The DNA was then amplified by PCR by using the oligonucleotide primers.

```
SEQ ID 1 - 5' CTG CGT GCG AAG TGA AGG ACG TTT GTG TTG 3'    (Forward)

SEQ ID 2 - 5' GAC CCC CAT CAC CCC TGT GTA ACT GAC TTC 3'    (Reverse)

SEQ ID 3 - 5' TGC CTG GAG CCC CTG GTG TCC CTG GAG AGC 3'    (Forward)

SEQ ID 4 - 5' TGC CTC GTC CGC ATT CAC CCT TCA GAC TGC 3'    (Reverse)
```

The sample were denatured at 95° C. for 5 minutes followed by 28 cycles of denaturation (95° C., 1 minutes), annealing (70° C., 1 minute), extension (72° C., 1 minute) and a final extension of 7 minutes at 72° C. in a PE GeneAmp PCR System 9600. This reaction produced a DNA fragment of 459 bp. The PCR product was purified from band cut out of agarose gel using a Qiaquick gel extraction kit (Qiagen) and both the strands of the PCR product were directly sequenced using gel terminator chemistry on an ABI Prism 377 automated DNA sequencer with PCR prisms. The PCR products were shown to be identical to the human SP-A2 mRNA, complete CDS sequence in the databse (accession no. M68519), submitted by Katyal. et al [Katyal, S. L., Singh, G. and Locker, Characterization of a second human pulmonary surfactant-associated protein SP-A gene. Am. J. Respir. Cell Mol. Biol. 1992; 6: 446-452] except for the previously mentioned 2 single base changes as listed in table 1.

EXAMPLE 2

Nucleotide Sequence of the Allelic Variant of SP-A2 Gene.

The nucleotide seq. of the allelic variant of SP-A 2 gene derived using the method as described in example 1. In the above sequence the 2 SNP's as given in table 1 are at nucleotide position 1649 and 1660.

EXAMPLE 3

Patients with the A allele at the 1660 position are at nearly zero risk for pulmonary tuberculosis disease. A method as described in example 1 is applied to a series of DNA samples extracted from pulmonary tuberculosis positive individuals and normal controls. There is observed a statistically significant difference (At position 1649 p=0.1320 and at position 1660 p=0.0000) in the frequency distributions of the SNP haplotypes generated using SNP in normal and pulmonary tuberculosis patient SP-A2 chromosome. The results obtained are summarized in Table III below:

TABLE III

| | SNP (G vs C) at 1649 position | SNP (G vs A) at 1660 position |
|---|---|---|
| ODDS'RATIO (pulmonary tuberculosis patient vs Normal) | 1.576<br>0.8696 < O.R. < 2.8564 | 8.9412<br>3.3136 < O.R. < 24.126 |
| Chi-square | 2.261 | 24.175 |
| p-value | 0.1320 | 0.0000 |

A strong association of G (at 1649 position) and G (at 1660 position) haplotypes with pulmonary tuberculosis disease chromosome indicated that SP-A2 alleles with the G (at 1649 position) and G (at 1660 position) haplotypes are predisposed to the disease. Therefore, these SNP haplotypes in the human SP-A2 gene could be used as a method of establishing individual risk to pulmonary tuberculosis. The association of G (at 1649 position) and G (at 1660 position) haplotypes with the pulmonary tuberculosis disease was studied in Indian population. However, C (at 1649 position) and A (at 1660 position) haplotypes being at low risk and G (at 1649 position) and G (at 1660 position) haplotypes being at high risk for pulmonary tuberculosis disease, can be expected to hold true for other human population also.

EXAMPLE 4

Nucleic Acid Vector Containing the SP-A2 Variant Sequences.

Expression vectors and host cells transformed with allelic variants of the SP-A2 gene, containing one or more polymorphic sites as listed in Table I can be proposed, for example as detailed below.

Allelic variant of SP-A2 gene can be expressed in an expression vector in which the variant gene is operably linked to a native or other promoter. Usually the promoter is an eukaryotic promoter for expression in mammalian cell. The transcription regulation sequence typically includes a heterologous promoter and optionally an enhancer which is recognised by the test. The structure of an appropriate promoter, for example, Trp, Lac, phage promoter, glycolytic enzyme promoters and tRNA promoter depends on the host selected. Commercially available expression vectors can also be used. The means of introducing the expression construct into a host cell will depend on particular construct and the target host. Suitable means include fusion, conjugation, transfection, transduction, electroporation or injection. A wide variety of host cells can be employed for expression of the variant gene, both prokaryotic and eukaryotic. Suitable host cells include bacteria such as *E. coli*, Yeast, filamentous fungi, insect cells, mammalian cells, typically immortalised example, mouse, CHO, human and monkey cell lines and derivatives thereof. Preferred host cells are able to process the variant gene product to produce an appropriate mature polypeptide.

Advantages

The invention shall be useful to establish genotype or base variation of SP-A2 gene. The information may be useful for molecular diagnosis, prediction of an individual's disease susceptibility to pulmonary tuberculosis, prognosis and/or the genetic analysis of SP-A2 gene in a population. The frequency of these variants can also be used to predict the prevalence of pulmonary tuberculosis disease among various populations.

All publications and patent applications mentioned in the specification are indicative of the level of those skilled in the art to which this invention pertains. The contents of all publications, patents and patent applications are herein incorporated by reference to the same extent as if each individual publication, patent or patent application was specifically and individually indicated to be incorporated by reference.

What is claimed is:

1. A method for predicting the susceptibility of an individual to pulmonary tuberculosis, said method comprising:
   a) amplifying genomic DNA of pulmonary tuberculosis patients and normal control individuals using oligonucleotide primers for PCR amplification of the polymorphic site containing A or G base region containing exon-4 of human SP-A2 gene to obtain an amplified product,
   b) sequencing the amplified PCR product and identifying the sequence variation computationally by comparing it with the human SP-A2 gene,
   c) establishing the association of C and G haplotypes as defined by the nucleotide present at position 1649 and 1660, with pulmonary tuberculosis, based on the haplotype frequency distribution in normal individuals and tuberculosis patients, and
   d) predicting the risk or susceptibility to pulmonary tuberculosis based on the haplotype present at the polymorphic sites in the said individual, wherein a haplotype with C at 1649 position and A at 1660 position is at low risk and a haplotype with G at 1649 position and G at 1660 position is at high risk for the disease.

2. A method as claimed in claim 1 wherein the oligonucleotide primers are SEQ ID NOS: 1 and 2 or SEQ ID NOS: 3 and 4.

3. A method of detection of human SP-A2 gene variants comprising:
   (a) amplifying genomic DNA of pulmonary tuberculosis patients and normal control individuals using the primers SEQ ID NOS: 1 and 2 or SEQ ID NOS: 3 and 4 for SP-A2 Exon 4;
   (b) sequencing the amplified PCR product and identifying the sequence variation computationally by comparing it with the already existing sequence of human SP-A2 gene;
   (c) screening normal control individuals and pulmonary tuberculosis patients;
   (d) computing the frequency of G/C haplotypes at 1649 position and A/G haplotypes at 1660 position;
   (e) establishing the association of G (at 1649 position) and G (at 1660 position) haplotypes with the pulmonary tuberculosis disease based on their frequency distribution in normals and pulmonary tuberculosis patients; and
   (g) predicting the risk or susceptibility to pulmonary tuberculosis based on the haplotype present at the polymorphic sites in the individual tested, C (at 1649 position) and A (at 1660 position) haplotypes being at low risk and G (at 1649 position) and G (at 1660 position) haplotypes at high risk to the disease.

* * * * *

```
                        SEQUENCE LISTING

<160> NUMBER OF SEQ ID NOS: 4

<210> SEQ ID NO 1
    <211> LENGTH: 30
    <212> TYPE: DNA
    <213> ORGANISM: Artificial Sequence
    <220> FEATURE:
    <223> OTHER INFORMATION: A forward primer for identification of allelic
          variants of SP-A2 gene

<400> SEQUENCE: 1
ctgcgtgcga agtgaaggac gtttgtgttg                                       30

<210> SEQ ID NO 2
    <211> LENGTH: 30
    <212> TYPE: DNA
    <213> ORGANISM: Artificial Sequence
    <220> FEATURE:
    <223> OTHER INFORMATION: A reverse primer for identification of allelic
          variants of SP-A2 gene

<400> SEQUENCE: 2 gaccccatc accctgtgt aactgacttc                                         30

<210> SEQ ID NO 3
    <211> LENGTH: 30
    <212> TYPE: DNA
    <213> ORGANISM: Artificial Sequence
    <220> FEATURE:
    <223> OTHER INFORMATION: A forward primer for identification of allelic
          variants of SP-A2 gene

<400> SEQUENCE: 3
tgcctggagc ccctggtgtc cctggagagc                                       30

<210> SEQ ID NO 4
    <211> LENGTH: 30
    <212> TYPE: DNA
    <213> ORGANISM: Artificial Sequence
    <220> FEATURE:
    <223> OTHER INFORMATION: A reverse primer for identification of allelic
          variants of SP-A2 gene

<400> SEQUENCE: 4
tgcctcgtcc gcattcaccc ttcagactgc                                       30
```